(12) United States Patent
Headrick et al.

(10) Patent No.: US 12,320,791 B2
(45) Date of Patent: Jun. 3, 2025

(54) CREATING MASS FLOW PARITY IN A VARIANT MULTI-CHANNEL SAMPLING SYSTEM

(71) Applicant: Picarro, Inc., Santa Clara, CA (US)

(72) Inventors: Jeffrey Michael Headrick, Alamo, CA (US); Wei Jian Chin, Sunnyvale, CA (US); Chris W. Rella, Sunnyvale, CA (US)

(73) Assignee: Picarro, Inc., Santa Clara, CA (US)

( * ) Notice: Subject to any disclaimer, the term of this patent is extended or adjusted under 35 U.S.C. 154(b) by 0 days.

(21) Appl. No.: 18/115,534

(22) Filed: Feb. 28, 2023

(65) Prior Publication Data

US 2023/0204553 A1 Jun. 29, 2023

Related U.S. Application Data

(63) Continuation of application No. 16/691,222, filed on Nov. 21, 2019, now abandoned.

(51) Int. Cl.
*G01N 33/00* (2006.01)
*G01F 5/00* (2006.01)
*G01F 15/00* (2006.01)

(52) U.S. Cl.
CPC ......... *G01N 33/0016* (2013.01); *G01F 5/005* (2013.01); *G01F 15/005* (2013.01)

(58) Field of Classification Search
CPC .... G01N 33/0016; G01F 15/005; G01F 5/005
USPC ....................................... 73/863.03
See application file for complete search history.

(56) References Cited

PUBLICATIONS

Text version of sierra instruments webpage (Year: 2019); https://www.sierrainstruments.com/blog/?complete-guide-gas-mixing-blending-sierra-instruments; Complete Guide to Gas Mixing and Blending | Sierra Instruments; Feb. 6, 2019.*

* cited by examiner

*Primary Examiner* — Alexander A Mercado
*Assistant Examiner* — Rodney T Frank
(74) *Attorney, Agent, or Firm* — LUMEN PATENT FIRM

(57) ABSTRACT

An equal mixture of gas flows from multiple inputs is provided to gas analysis instrumentation, despite the unequal gas flow properties of the inputs often seen in practice. E.g., due to unequal input sample line lengths. We provide gas flow symmetry into a gas manifold that provides the output(s) to the gas analysis instrument(s). Such symmetry has two parts—equal gas flow properties from a set of reference points (one reference point for each input) to the manifold, and equal pressures at the reference points. Such equal pressures can be provided for unequal input gas flow properties by having a bypass valve for each input controlled so as to equalize the pressures.

19 Claims, 9 Drawing Sheets

CREATING MASS FLOW PARITY IN A VARIANT MULTI-CHANNEL SAMPLING SYSTEM

CROSS REFERENCE TO RELATED APPLICATIONS

This application is a continuation of U.S. patent application Ser. No. 16/691,222, filed on Nov. 21, 2019, and hereby incorporated by reference in its entirety.

FIELD OF THE INVENTION

This invention relates to gas handling for gas analysis instrumentation.

BACKGROUND

A gas analyzer is an instrument designed to measure the concentration of one or more specific compounds in a gas sample. A typical application of such a gas analyzer is to use a single system to monitor the gas concentration at multiple locations. The key metric for this application is the measurement cycle time, which is defined as the time needed to obtain an accurate representation of the gas at each inlet point. This application is typically achieved by incorporating the gas analyzer into a multichannel sampling system. Perhaps the simplest implementation of a multichannel sampling system is a many-to-one valve manifold, where the gas analyzer is attached to the common output port, and sampling tubes are connected to the multiple inlet ports. Each of the sampling tubes is installed in different locations, often with different lengths of tubing. In the most common mode of operation, the valve manifold is controlled such that one and only of the input ports is pneumatically connected to the output port. In this way, the gas analyzer can sequentially analyze the gas at each of the input ports. Typically, the valve manifold is realized either via a tree of 3-way solenoid or pneumatically controlled valves, or via a rotary valve.

There are several disadvantages of this simple implementation:

1. When one location is being measured, the others are not. In other words, the temporal duty factor of measurement at a given location is given by 1/N, where N is the number of ports on the sampler.
2. When a port is not being measured, there is no flow in the tube. In such a stagnant sample, the concentration in the tube is dominated by adsorption and desorption effects on the surface of the tubing and potentially by diffusion through the tubing walls. When this port is sampled again, the concentration reported does not represent the input concentration for a significant amount of time, thus increasing the total measurement cycle time.
3. For most implementations of the valve manifold, during transitions when the valve manifold is changing state, there is a rapid and significant change in the impedance of the flow path, leading to pressure and flow transients that are often highly disruptive to the gas analyzer, leading to spurious results that must be ignored, and further extending the measurement cycle time.
4. Many gas analyzers are limited in the maximum gas flow that they can consume. This limited gas flow in turns limits the gas flow through the sampling manifold, which in turn increases the total measurement cycle time.

SUMMARY

One may address disadvantage #2 by supplying an auxiliary pump to draw on all the sampling lines continuously, which continuously refreshes the sample in the tubing.

One approach to address disadvantage #1 would be to sample from multiple input ports simultaneously. The simplest and most generally desirable outcome would be that the concentration of the target compound as measured by the gas analyzer would be the simple arithmetic average of the input concentrations present on the active input ports. This average is achieved when the flow contribution from each input port to the total analyzer flow is equal. One might imagine that opening multiple ports simultaneously in standard sampling systems would deliver this condition. In practice, however, this condition is extremely difficult to achieve, as it requires an equivalent impedance to gas flow in each of the sampling ports. The simple act of having different length sampling lines, and/or any asymmetry in the valve manifold, will lead to unbalanced flows, which will then lead to an overemphasis of the high flow ports in the total, and an underemphasis of low flow ports.

It would therefore be desirable to design a multichannel sampling system that can measure a) each port independently or b) multiple ports simultaneously (with balanced flow), maintaining flow on all ports even when not active, and without flow or pressure transients that disrupt the gas analyzer, in a way that minimizes the measurement cycle time, even for low flow gas analyzers.

The main technical idea of this work is to ensure gas flow symmetry into a gas manifold that provides the output(s) to the gas analysis instrument(s). Such symmetry has two parts—equal gas flow properties from a set of reference points (one reference point for each input) to the manifold, and equal pressures at the reference points. Such equal pressures can be provided for unequal input flow rates by having a bypass valve for each input controlled so as to equalize the pressures.

The following technical analysis provides further details on this symmetry point. In a thermally stable environment, mass flow rate Q through a gas line of length L is proportional to pressure drop $\Delta P$ as follows $$Q \propto \frac{\Delta P}{L}. \tag{1}$$

In a simple multichannel gas sampling system with a common mixing volume, one typically has equal pressure drops for each input, but unequal gas line lengths for each input. Therefore the resulting mass flows will be unequal. Furthermore, it may not be reasonable to make the conductance of the gas lines equal (e.g., they may be part of a customer installation that cannot be altered). The above equation holds where the pressure drop $\Delta P$ is small compared to the inlet pressure at the upstream end of the line. For larger pressures, a more complex relationship holds due to the compressibility of the gas, although the mass flow remains a monotonically increasing function of the pressure drop. For the purposes of this description, we will continue to use the linear approximation of small pressure drops, with the understanding that the expressions can be expanded to account for the compressibility of the gas. Finally, we note that the head pressure at the upstream end of different gas lines might also be different, and might also be variable, leading to additional flow variability from line to line and over time.

To solve this problem, we split off the sample paths of each channel prior to a common mixing volume (CV). The paths that face the CV are mechanically identical across all channels. The diverted bypass paths terminate at channel-dedicated proportional valves. Without the proportional valves, splitting the sample paths would merely lead to equal L and unequal ΔP from the split points to the CV. Thus equalizing the pressures at the split points is the primary task of the automatic system controller.

In some embodiments thermal stability across all inputs is not achievable and pressure and temperature need to be measured at each split point and in the CV to adequately compare the different mass flow rates that define the system. Mass flow rate has units of standard liters per minute (SLPM) which is a volumetric flowrate corrected to a standard temperature and pressure (STP). Multiplying a Q with units of SLPM by the density of the moving fluid at STP results in a value with units of mass per time. Above we have shown that mass flow rate Q can be related to pressure drop ΔP however, it should be made clear that pressure drop needs to be normalized to STP before interpreting the results as a mass flow rate. To properly relate $Q_{S,x}$ (mass flow to the CV for channel x) in terms of measured quantities ($P_c$=CV pressure, $T_c$=CV Temperature, $P_x$=pressure at the input split point for channel x, $T_x$=temperature at the input split point for channel) we can use the following approximate relationship:

$$Q_{S,x} \propto \Delta P_{STP} = (P_C - P_x) \cdot \frac{P_{Ave}}{P_{STP}} \cdot \frac{T_{STP}}{T_{Ave}} \quad (2)$$

where the subscript 'Ave' represents the simple average of the physical conditions measured at 'C' and 'x'. The 'Ave' values are the anchor points from where the STP correction for the system inputs are executed. From the above expressions we see that if one has the ability to control the values of $P_X$ while monitoring the value $P_C$ then parity can be established across all $Q_{S,X}$ regardless of the upstream variances. In this work the actuator to be used to control $P_X$ is the channel dedicated bypass proportional valves. By varying the adjustments of these valves we can control the pressures at the splits, $P_X$, and by association, the mass flow rates, $Q_{S,X}$. This method achieves the goal of creating mass flow parity in varying multi-channel sampling systems.

Equal relative mass flow rate between two or more channels is what is required to achieve equal gas mixing. We note that to measure the absolute flow rate, a further step is needed, which is to characterize the conductance of the flow system—i.e., to determine the proportionality between flow and pressure in Eq. 2.

DETAILED DESCRIPTION

Figure 1:
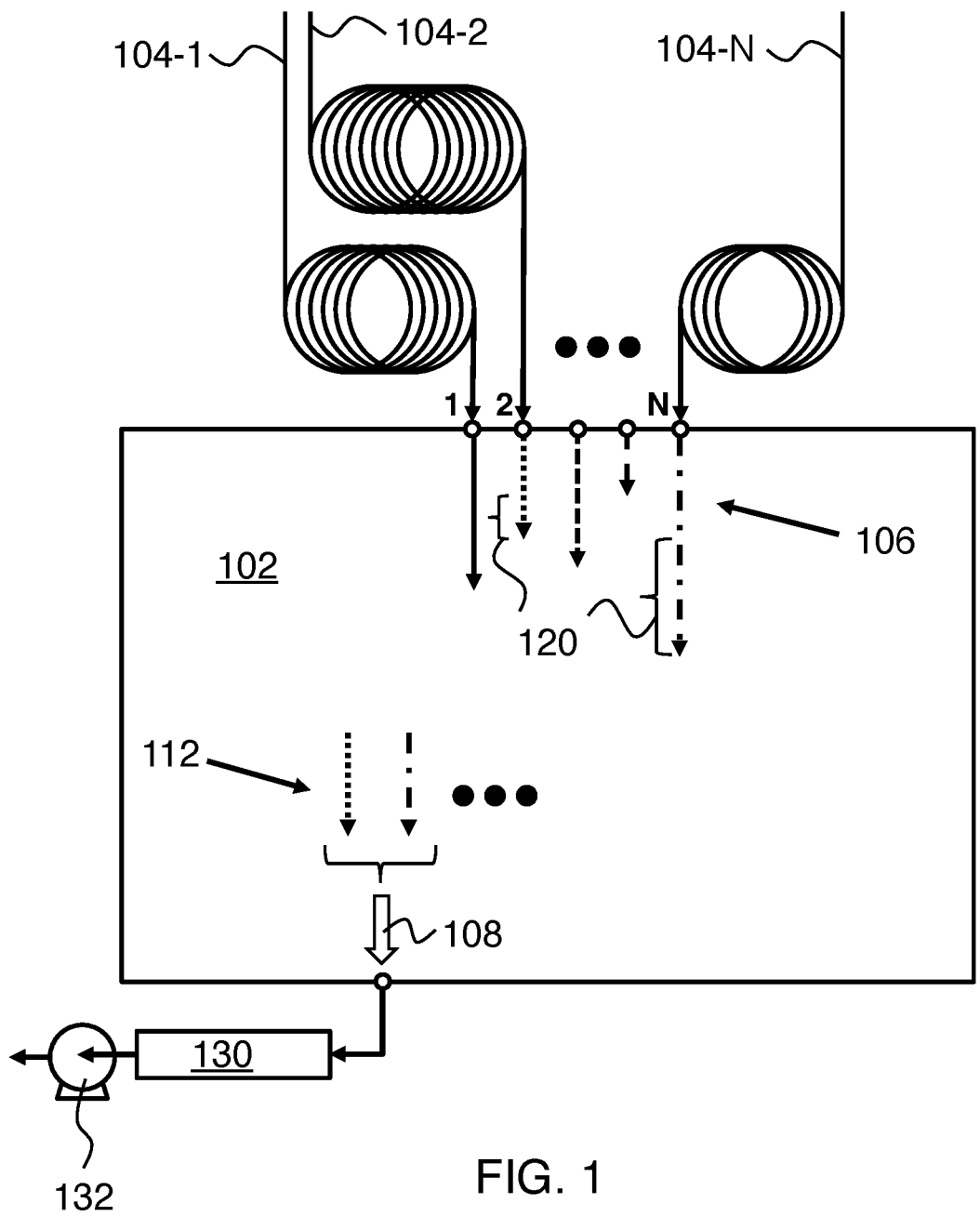
FIG. 1 shows a first operating mode of embodiments of the invention.

To better appreciate the present invention, it will be helpful to consider the functionality provided by various operating modes of the gas flow control system prior to describing how the gas flow system can be implemented in practice. FIG. 1 shows a first operating mode. Here 104-1, 104-2, . . . , 104-N are sample input lines leading to gas flow system 102. As indicated above, an important practical issue is that these sample lines typically have unequal properties that affect the gas flows they provide, making the input gas flows unequal. This is schematically shown by input gas flows 106 having arrows of different lengths, with longer arrows corresponding to higher gas flow rates.

In this mode, the output of gas flow system 102 is a combined gas flow 108 including an equal mixture 112 of gas flows from a selected two or more of the system inputs. Here the equal mixture is schematically shown by equal length arrows in 112, despite the unequal input flows for the components of the mixture. This combined gas flow is provided to gas analysis instrumentation 130. For completeness, a pump 132 is shown that draws the combined gas flow through gas analysis instrumentation 130.

Here "an equal mixture of gas flows from a selected two or more of the system inputs in the combined gas flow" means that the combined gas flow has equal contributions O1, O2, O3 (O1=O2=O3) from the selected system inputs (e.g., inputs 1, 2, 3 of a 5 input system) even though flow rates at the corresponding inputs (I1, I2, I3) may not be equal (I1< >I2 and/or I2< >I3 etc.). Such inequality of the input flow rates most commonly comes from unequal sample input line lengths which usually cannot be made equal in practice. This work provides various ways to automatically compensate for unequal input flow rates.

A "combined gas flow" is one or more gas flows provided by the system as its output(s). If the combined gas flow is a single output, then that output is an equal mixture of the relevant inputs as described above. If the combined gas flow is multiple outputs (e.g., as in some examples below), then each constituent output is an equal mixture of the relevant inputs as described above. "gas analysis instrumentation" is one or more gas analysis instruments.

Accordingly, an embodiment of the invention includes a gas flow system as described above. More specifically, the gas flow system is an automatically controlled gas flow system configured to combine all or a portion of gas flows from one or more system inputs (e.g., 1, 2, . . . , N on FIG. 1) into a combined gas flow provided to the gas analysis instrumentation. The automatically controlled gas flow system also has one or more operating modes that include a first operating mode where the combined gas flow includes an equal mixture of gas flows from a selected two or more of the system inputs (e.g. 112 on FIG. 1). The automatically controlled gas flow system in the first operating mode automatically compensates for unequal input gas flow rates at the selected two or more of the system inputs.

Figure 2:
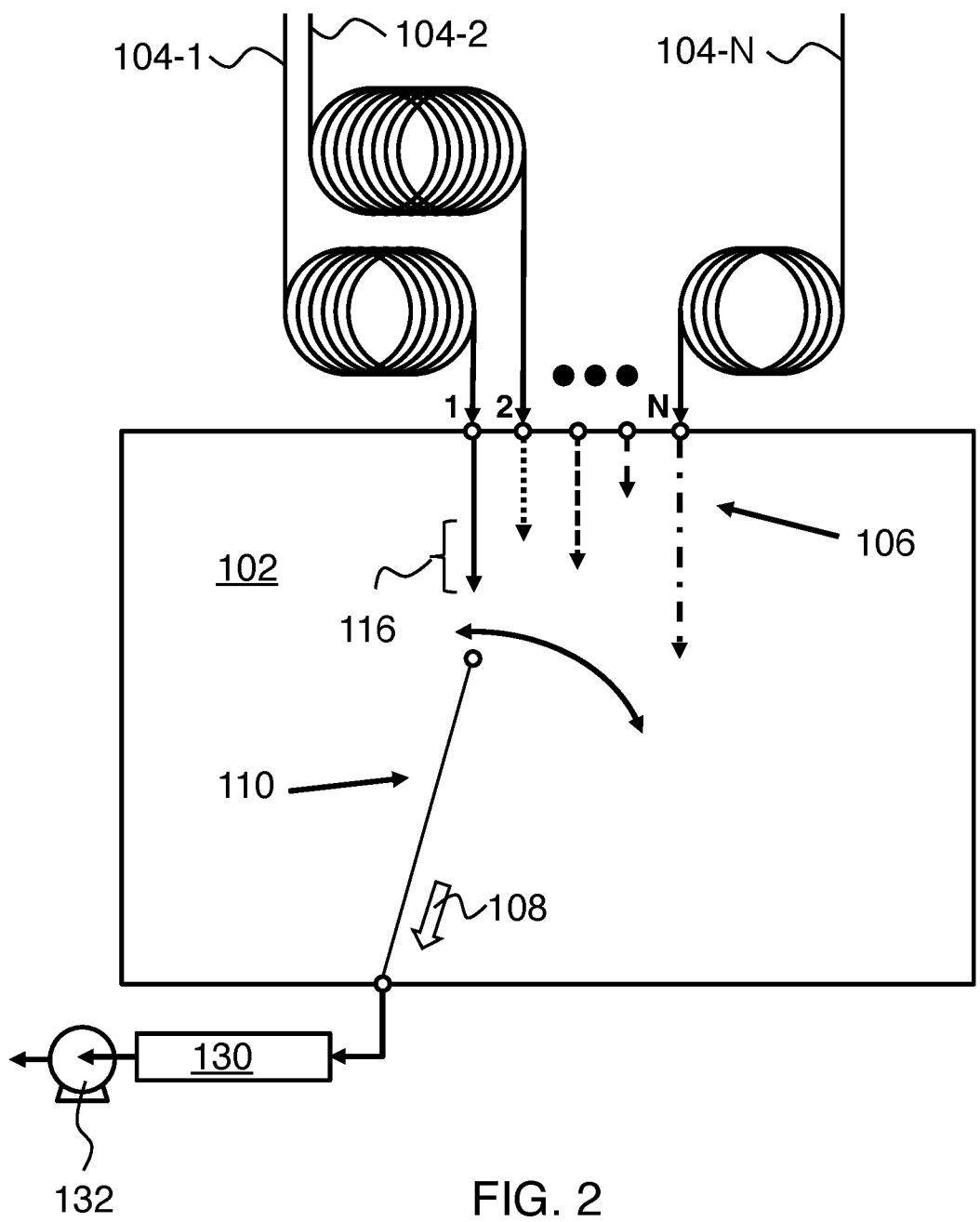
FIG. 2 shows a second operating mode of embodiments of the invention.

FIG. 2 shows a second operating mode that provides a switchable gas flow from a selected system input to the gas analysis instrumentation. Here this switching action is schematically shown by line 110 and the curved double-headed arrow showing how it can be connected to any one of the inputs.

The first and second operating modes suffer from disadvantage #2 above, which can be expressed more generally as an undesirable dependence of input flow rates on the switching state of the automatically controlled gas flow system. E.g., flow rates at unselected inputs can be zero, leading to undesirable effects of stagnant gas lines as indicated above. On FIG. 2, this dependence is schematically shown as flow rate range 116 for input 1. E.g., the flow rate at this input could be zero if the input is not selected by switch 110. All inputs would have such input flow rate variability, but only one range is shown on the figure to avoid clutter. Similarly, input flow rate dependence on FIG. 1 is shown as flow rate ranges 120 on inputs 2 and 5. E.g., the flow rate at these inputs could be zero if these input were not included in mixture 112. All inputs would have such input flow rate variability, but ranges for only two of the inputs are shown on the figure to avoid clutter.

Figure 3:
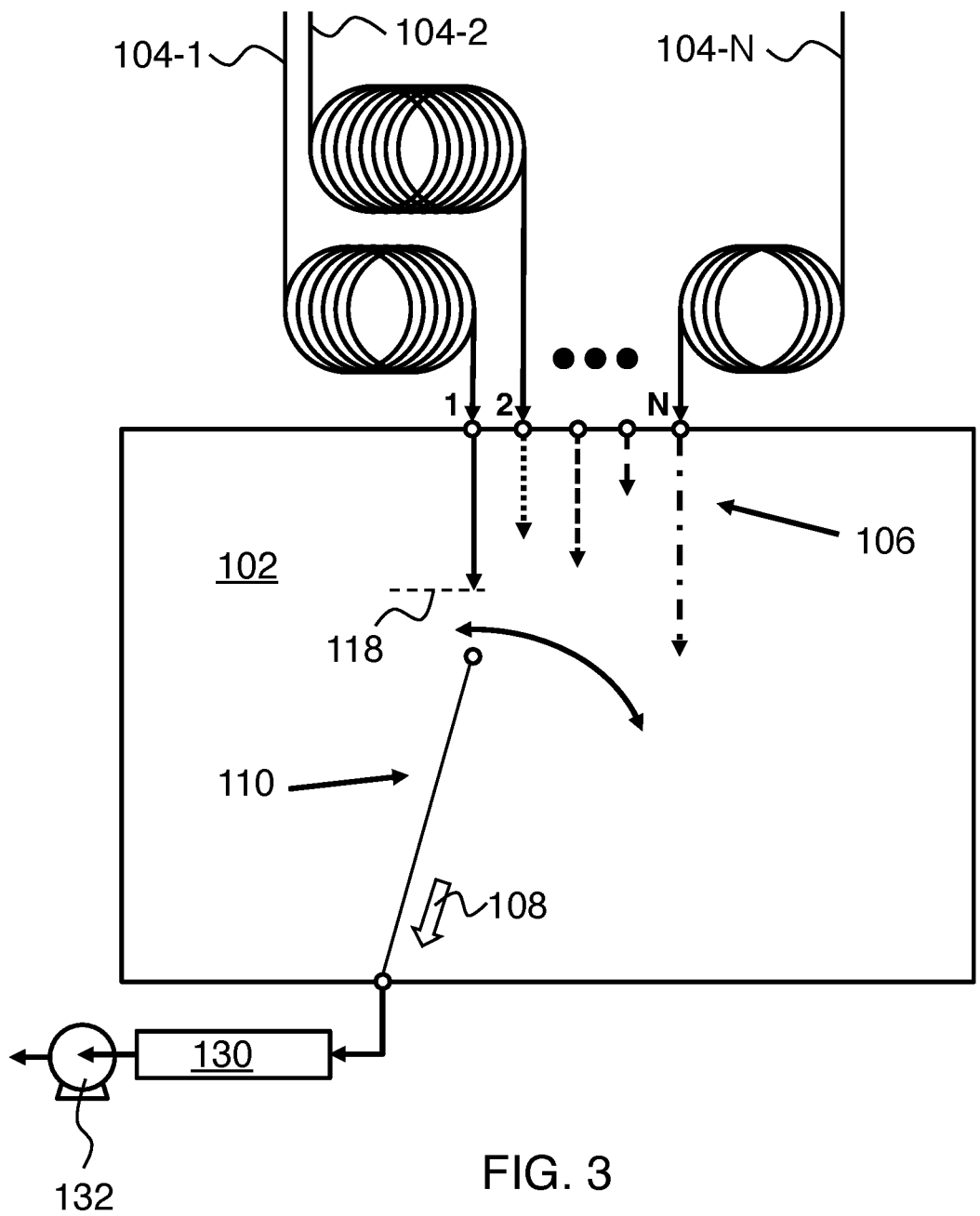
FIG. 3 shows a third operating mode of embodiments of the invention.

FIG. 3 shows a third operating mode. This mode has switchable gas flow from a selected system input to the gas analysis instrument as in the example of FIG. 2. Furthermore it has constant gas flow at each of the system inputs independent of a switching state of the automatically controlled gas flow system. Here this constancy of the input flow rates is schematically shown by dashed line 118, with the meaning that the flow rate of input 1 does not depend on whether or not input 1 is connected to the output. All inputs would have such constant input flow rates, but this is only shown for one input on the figure to avoid clutter.

Figure 4:
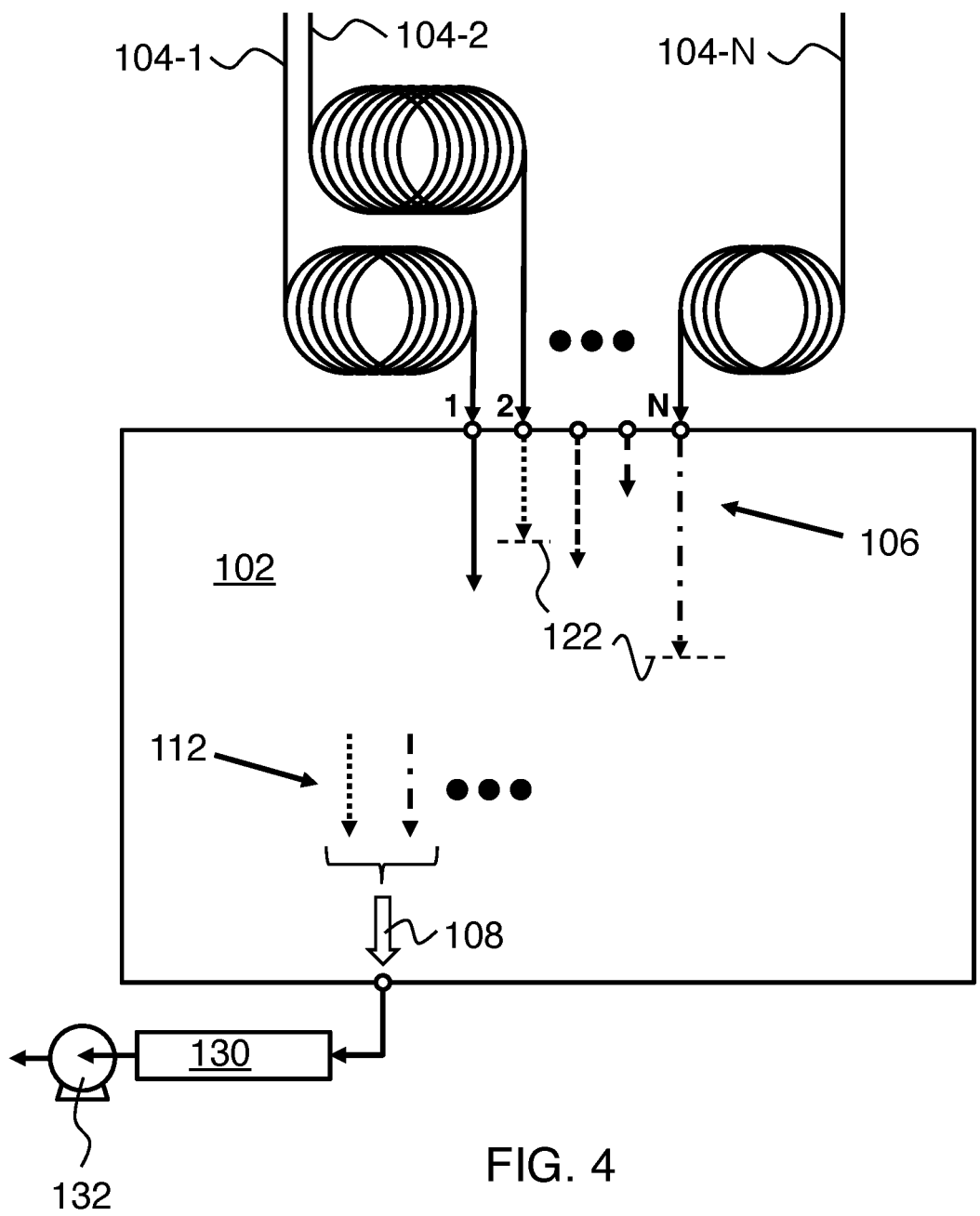
FIG. 4 shows a fourth operating mode of embodiments of the invention.

FIG. 4 shows a fourth operating mode. This mode provides an equal mixture of gas flows from a selected two or more of the system inputs as in the example of FIG. 1. The automatically controlled gas flow system in the fourth operating mode automatically compensates for unequal input gas flow rates at the selected two or more of the system inputs. Furthermore, it has constant gas flow at each of the system inputs independent of which of the system inputs are selected. Here this constancy of the input flow rates is schematically shown by dashed lines 122, with the meaning that the flow rates of inputs 2 and 5 do not depend on whether or not inputs 2 and 5 are mixed to provide the output. All inputs would have such constant input flow rates, but this is only shown for two inputs on the figure to avoid clutter.

Figure 5:
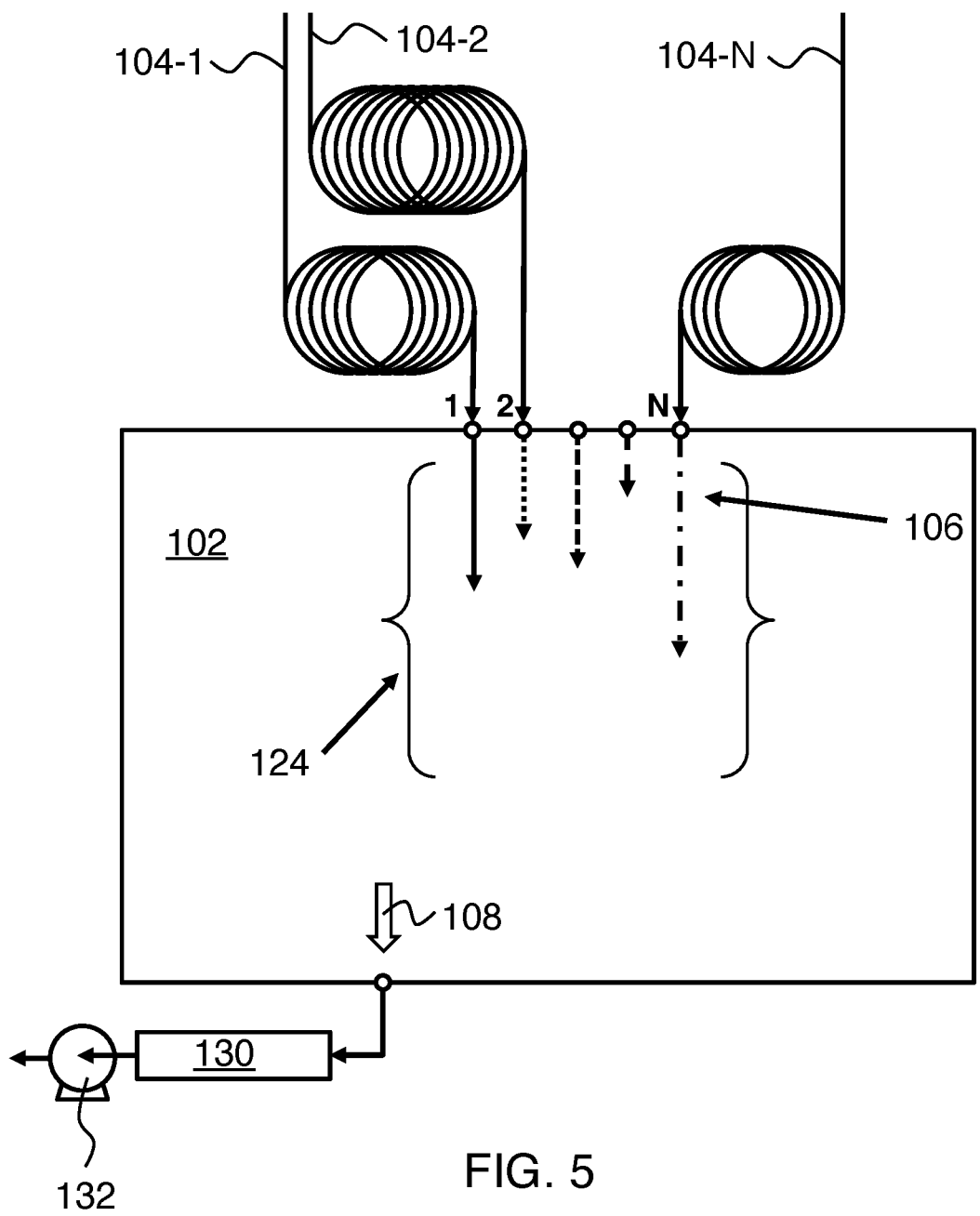
FIG. 5 shows an enhanced flow concept for embodiments of the invention.

Operating modes 3 and 4 address the issue of stagnant input gas lines for non-selected inputs, but disadvantages 3 and/or 4 can still be present. Accordingly, it is preferred for the automatically controlled gas flow system to provide an adjustable system gas flow rate in any of its operating modes without altering a combined gas flow rate provided to the gas analysis instrumentation. FIG. 5 schematically shows this concept. Here the idea is for the combined gas flow rate 108 to remain unaffected by changing the system gas flow rate (schematically shown as a range 124 for the input gas flow rates 106). The system gas flow rate is the total gas flow rate into the system via all of the system inputs combined. In practice this can be used to increase the input flow rates far above what the gas analysis instrumentation can accept, thereby alleviating disadvantages #3 and #4 above. Accordingly, it is convenient to refer to the concept of FIG. 5 as "enhanced flow".

Although consideration of all of the operating modes is helpful in appreciating the invention, it is not required for embodiments to have all operating modes. The only required operating mode is the first operating mode with an automatically provided equal mixture of two or more selected inputs at the output. Accordingly, embodiments of the invention can further include any combination of operating modes 2, 3, 4, and/or enhanced flow.

Figure 6:
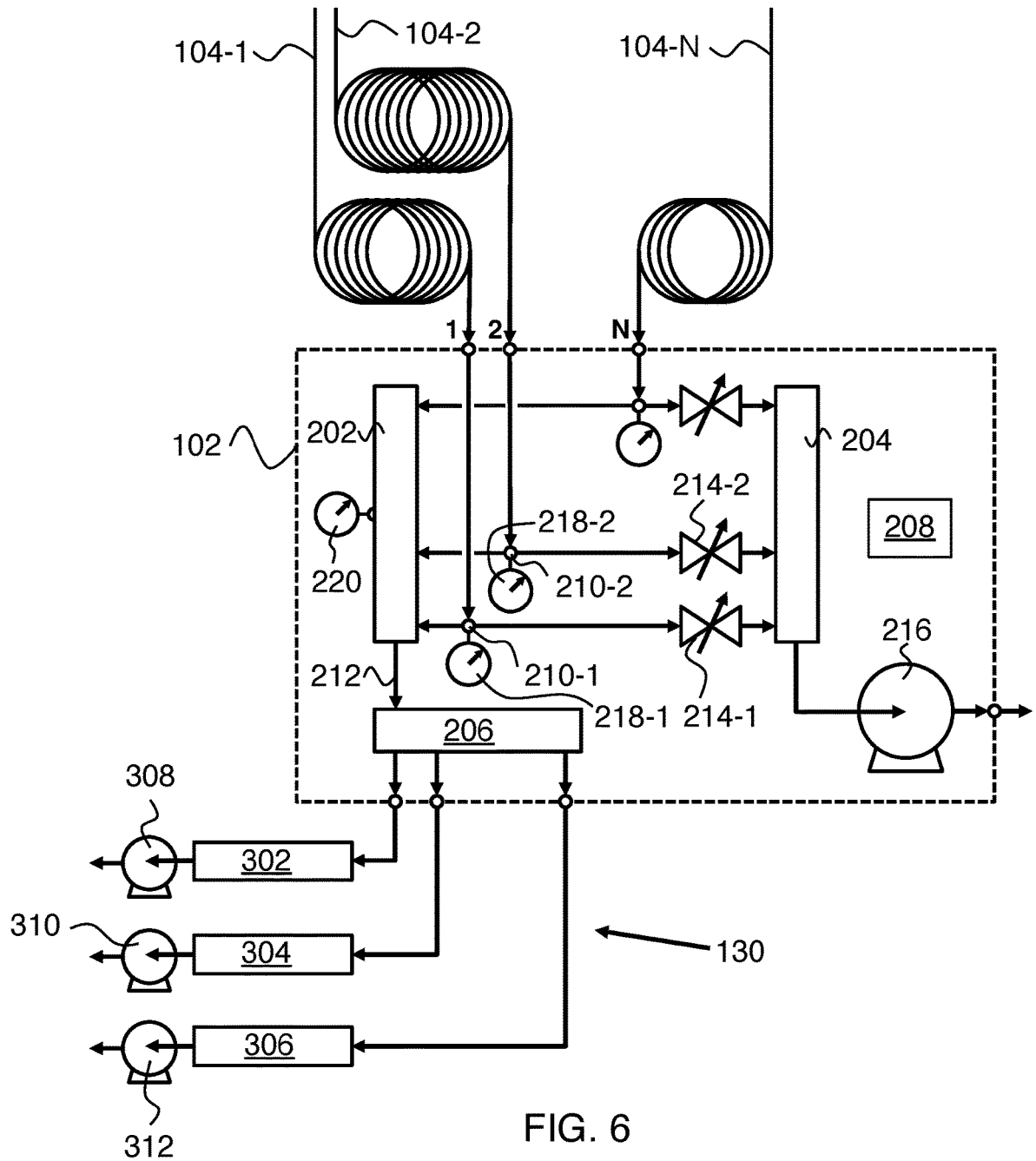
FIG. 6 shows a first embodiment of the invention.

FIG. 6 shows a first example of a gas flow system as described above. Here gas flow system 102 includes two or more gas flow Y-junctions (210-1, 210-2, . . . ), where each gas flow Y-junction is configured to receive sample gas from a corresponding sample input line (104-1, 104-2, . . . ) and configured to split the sample gas into first gas emitted from a first Y-junction output and second gas emitted from a second Y-junction output. Gas flow system 102 also includes a first gas manifold 202 configured to receive the first gas from all the first Y-junction outputs and having a common output 212 having an output gas flow, where part or all of the output gas flow is delivered as the combined gas flow to the gas analysis instrumentation 130. Here gas analysis instrumentation is shown as three gas analysis instruments 302, 304, 306 having corresponding pumps 308, 310, 312 by way of example. Any number of gas analysis instruments can be used.

Gas flow system 102 also includes two or more proportional valves (214-1, 214-2, . . . ), each proportional valve configured to receive the second gas from the second Y-junction output of a corresponding gas flow Y-junction. Gas flow system 102 also includes a second gas manifold 204 configured to receive the second gas from outputs of all the proportional valves and a gas pump 216 configured to draw gas from the second gas manifold 204 and exhaust it from the apparatus. Finally, gas flow system 102 also includes a system controller 208 configured to measure at least pressures at the first gas manifold and at each of the gas flow Y-junctions, and configured to control at least all of the proportional valves. Here 218-1, 218-2, . . . are the pressure sensors for the Y-junctions, and 220 is the pressure sensor for the first gas manifold. Connections from system controller 208 to the components of the system are not shown on the figure. In some cases, e.g., as described above, it is preferred for system controller 208 to also be configured to measure temperatures at the first gas manifold and at each of the gas flow Y-junctions.

In practice it is often desired to provide inputs to multiple gas analysis instruments as shown in the example of FIG. 6. Accordingly, preferred embodiments include a third gas manifold 206 to provide these multiple outputs. In general the third gas manifold has one input and two or more outputs, and is configured to receive the output gas flow of the first gas manifold. Here all of the outputs of the third gas manifold provide the combined gas flow to the gas analysis instrumentation. In examples below, we will see that gas from the third gas manifold can be partially diverted away from the gas analysis instrumentation.

In preferred embodiments, gas flow paths between the Y-junctions (210-1, 210-2, . . . ) and the first gas manifold 202 have the same gas flow properties for all the Y-junctions. Here gas flow paths have "the same gas flow properties" if equal pressure drops from inputs to outputs of the gas flow paths provide equal gas flow rates through the gas flow paths for gas of the same composition and temperature. A "gas manifold" is any arrangement of gas flow chambers and/or gas flow lines having two or more inputs and/or two or more outputs.

With the apparatus of FIG. 6, the first operating mode can be provided by ensuring equal pressures Pa>P1 at gas flow Y-junctions corresponding to each of the active system inputs and equal pressures Pi=P1 at gas flow Y-junctions corresponding to inactive system inputs. Here P1 is the pressure in the first gas manifold.

With the apparatus of FIG. 6, the second operating mode can be provided by ensuring a pressure Pa>P1 at a gas flow Y-junction corresponding to a selected system input and equal pressures Pi=P1 at gas flow Y-junctions corresponding to inactive system inputs. Here also, P1 is the pressure in the first gas manifold.

Figure 7:
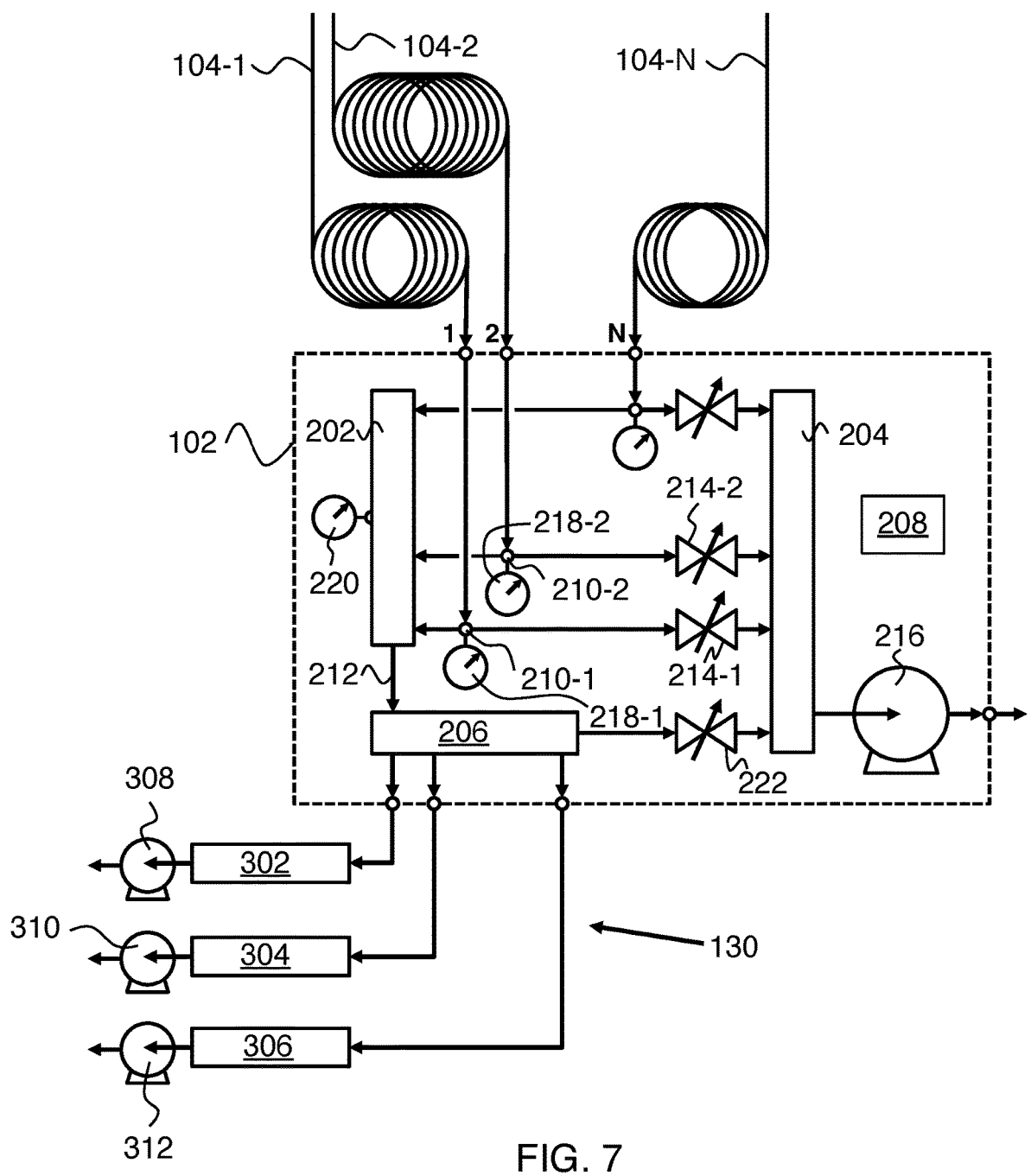
FIG. 7 shows a second embodiment of the invention.

The example of FIG. 7 differs from the example of FIG. 6 by the addition of a bypass proportional valve 222 connecting an output of third gas manifold 206 to an input of second gas manifold 204. Here the other outputs of the third gas manifold 206 provide the combined gas flow to the gas analysis instrumentation. Preferably system controller 208 is configured to adjust a flow rate of the output gas flow 212 from the first gas manifold without altering the combined gas flow rate provided to the gas analysis instrumentation 130 by adjusting the bypass proportional valve 222.

With the apparatus of FIG. 7, the first operating mode+ "enhanced flow" can be provided by ensuring equal pressures Pa>P1 at gas flow Y-junctions corresponding to each of the active system inputs and equal pressures Pi=P1 at gas flow Y-junctions corresponding to inactive system inputs. Here P1 is the pressure in the first gas manifold.

With the apparatus of FIG. 7, the second operating mode+"enhanced flow" can be provided by ensuring a pressure Pa>P1 at a gas flow Y-junction corresponding to a selected system input and equal pressures Pi=P1 at gas flow Y-junctions corresponding to inactive system inputs. Here also, P1 is the pressure in the first gas manifold.

Figure 8:
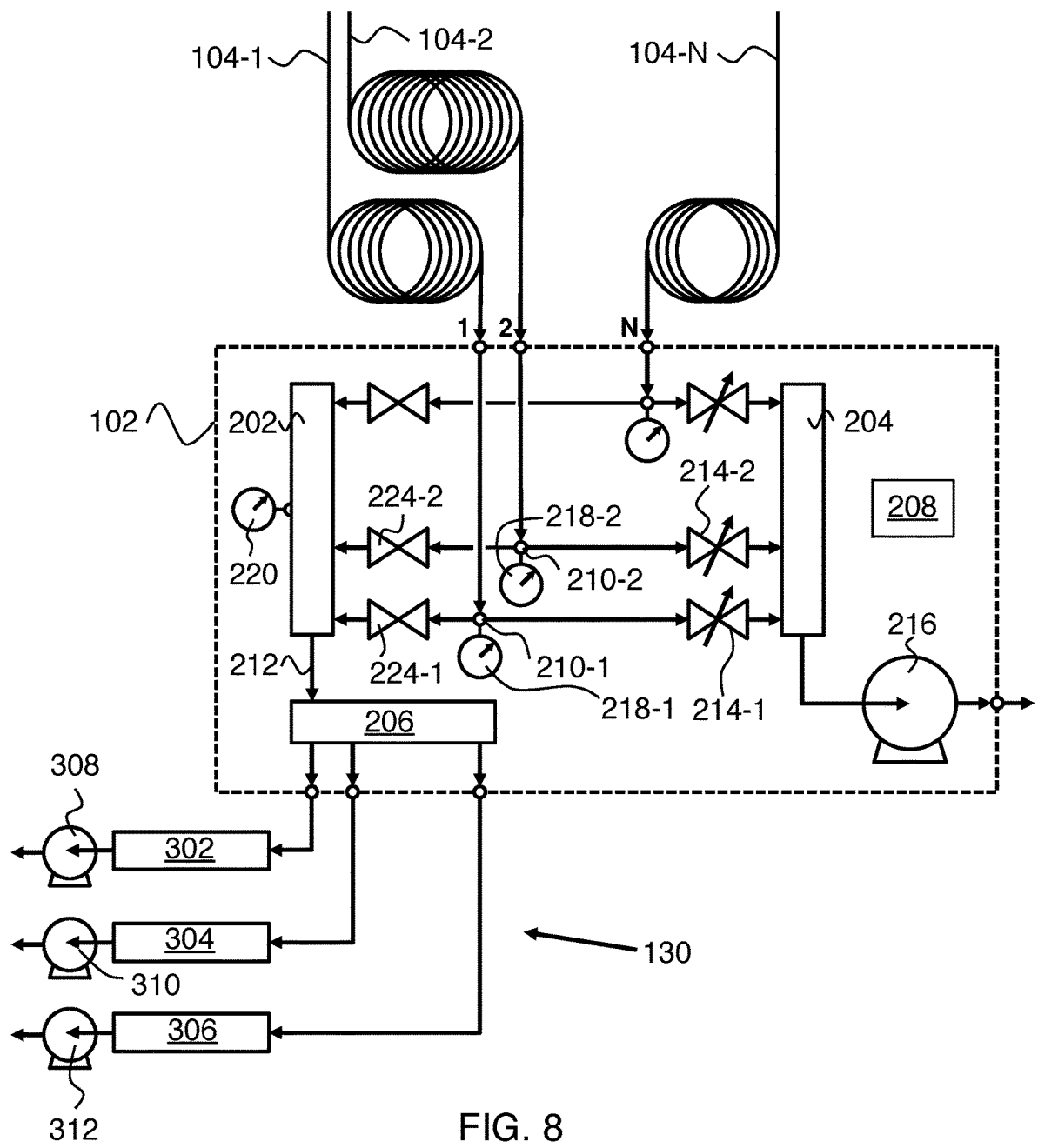
FIG. 8 shows a third embodiment of the invention.

The example of FIG. 8 differs from the example of FIG. 6 by the addition of two or more on-off valves (224-1, 224-2, . . . ), where each on-off valve is configured to switch gas flow on or off between a corresponding gas flow Y-junction and the first gas manifold 202.

With the apparatus of FIG. 8, the third operating mode can be provided by ensuring equal pressures Pa>P1 at all of the gas flow Y-junctions, and where the on-off valves are used to select a single gas flow to be provided to the gas analysis instrumentation. Here P1 is the pressure in the first gas manifold.

With the apparatus of FIG. 8, the fourth operating mode can be provided by ensuring equal pressures Pa>P1 at all of the gas flow Y-junctions, and where the on-off valves are used to select two or more gas flows to be provided to the gas analysis instrumentation in an equal mixture. Here also P1 is the pressure in the first gas manifold.

Figure 9:
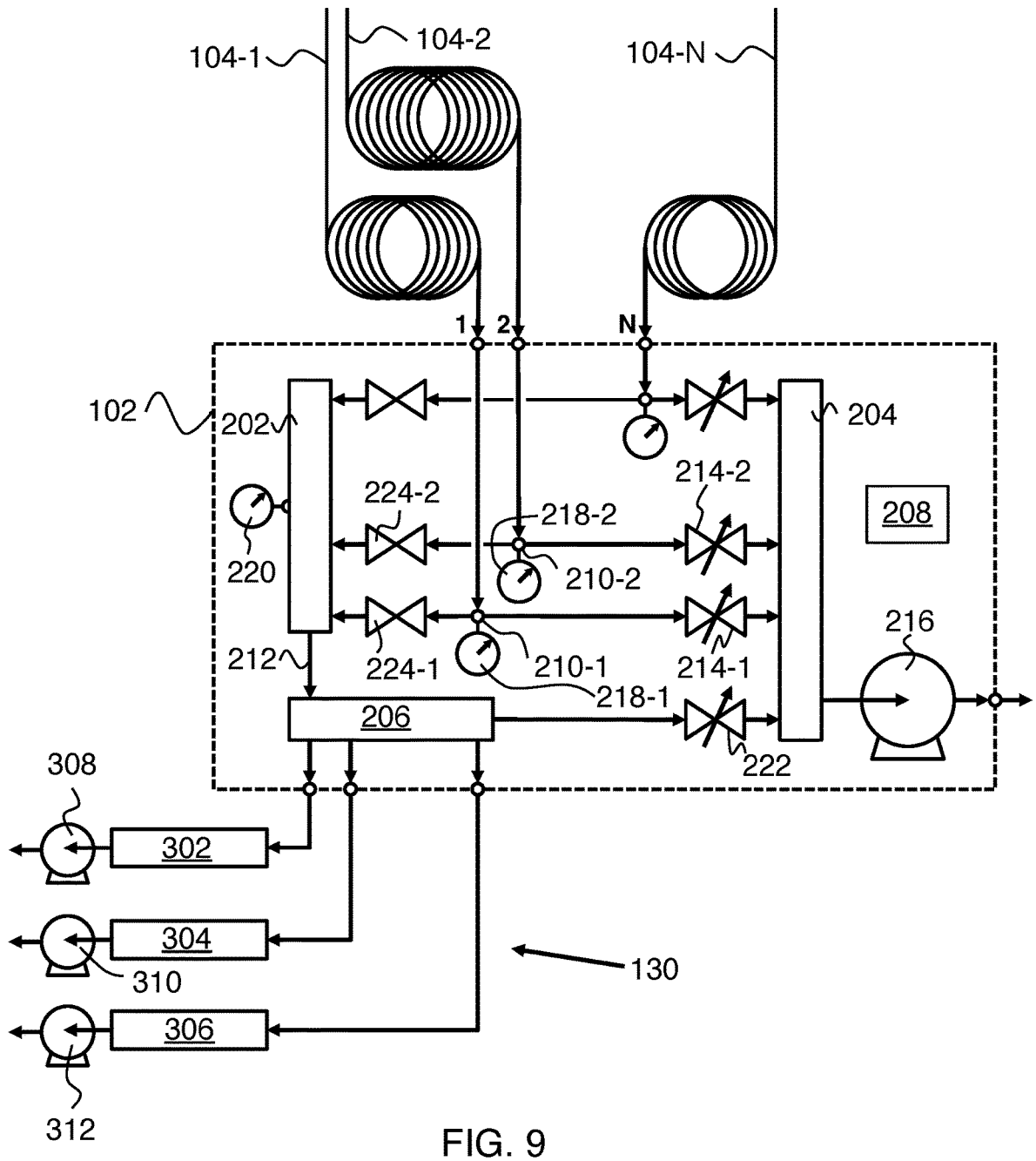
FIG. 9 shows a fourth embodiment of the invention.

The example of FIG. 9 differs from the example of FIG. 8 by the addition of a bypass proportional valve 222 connecting an output of third gas manifold 206 to an input of second gas manifold 204, as described above in connection with FIG. 7.

With the apparatus of FIG. 9, the third operating mode+ "enhanced flow" can be provided by ensuring equal pressures Pa>P1 at all of the gas flow Y-junctions, and where the on-off valves are used to select a single gas flow to be provided to the gas analysis instrumentation. Here P1 is the pressure in the first gas manifold.

With the apparatus of FIG. 9, the fourth operating mode+ "enhanced flow" can be provided by ensuring equal pressures Pa>P1 at all of the gas flow Y-junctions, and where the on-off valves are used to select two or more gas flows to be provided to the gas analysis instrumentation in an equal mixture. Here also P1 is the pressure in the first gas manifold.

The invention claimed is:

1. Apparatus for providing a gas sample to analysis instrumentation, the apparatus comprising: an automatically controlled gas flow system configured to combine all or a portion of gas flows from two or more system inputs into a combined gas flow provided to the gas analysis instrumentation; wherein the automatically controlled gas flow system has one mode of or more operating modes that include a first operating wherein the combined gas flow includes an equal mixture gas flows from a selected two or more of the system inputs; wherein the equal mixture of gas flows is provided by equalizing pressures of gas flows from the selected two or more that of have the system inputs that are provided to gas flow paths the same gas flow properties; wherein the pressures of gas flows are equalized using two bypass valves, wherein each system input is connected to a respective bypass valve.

2. The apparatus of claim 1, wherein the operating modes include a second operating mode having switchable gas flow from a selected system input to the gas analysis instrumentation.

3. The apparatus of claim 1, wherein the operating modes include a third operating mode having switchable gas flow from a selected system input to the gas analysis instrument with constant gas flow at each of the system inputs independent of a switching state of the automatically controlled gas flow system.

4. The apparatus of claim 1, wherein the operating modes include a fourth operating mode wherein the combined gas flow includes an equal mixture of gas flows from a selected two or more of the system inputs, and having constant gas flow at each of the system inputs independent of which of the system inputs are selected;
wherein the equal mixture of gas flows is provided by equalizing pressures of gas flows from the selected two or more of the system inputs that are provided to gas flow paths that have the same gas flow properties.

5. The apparatus of claim 1, wherein the automatically controlled gas flow system is configured to provide an adjustable system gas flow rate in any of its operating modes without altering a combined gas flow rate provided to the gas analysis instrumentation.

6. The apparatus of claim 1, wherein the automatically controlled gas flow system comprises:
two or more gas flow Y-junctions, each gas flow Y-junction configured to receive sample gas from a corresponding sample input line and configured to split the sample gas into first gas emitted from a first Y-junction output and second gas emitted from a second Y-junction output;
a first gas manifold configured to receive the first gas from all the first Y-junction outputs and having a common output having an output gas flow, wherein part or all of the output gas flow is delivered as the combined gas flow to the gas analysis instrumentation;
two or more proportional valves, wherein the proportional valves are the bypass valves, and wherein each proportional valve is configured to receive the second gas from the second Y-junction output of a corresponding gas flow Y-junction;
a second gas manifold configured to receive the second gas from outputs of all the proportional valves;
a gas pump configured to draw gas from the second gas manifold and exhaust it from the apparatus;
a system controller configured to measure at least pressures at the first gas manifold and at each of the gas flow Y-junctions, and configured to control at least all of the proportional valves.

7. The apparatus of claim 6, wherein gas flow paths between the gas flow Y-junctions and the first gas manifold have the same gas flow properties for all the gas flow Y-junctions.

8. The apparatus of claim 7, wherein a common pressure of the first gas manifold is P1, and wherein the first operating mode is provided by ensuring equal pressures Pa>P1 at gas flow Y-junctions corresponding to each of the active system inputs and equal pressures Pi=P1 at gas flow Y-junctions corresponding to inactive system inputs.

9. The apparatus of claim 7, wherein a common pressure of the first gas manifold is P1, and wherein a second operating mode is provided by ensuring a pressure Pa>P1 at a gas flow Y-junction corresponding to a selected system input and equal pressures Pi=P1 at gas flow Y-junctions corresponding to inactive system inputs.

10. The apparatus of claim 7, further comprising two or more on-off valves, each on-off valve configured to switch gas flow on or off between a corresponding gas flow Y-junction and the first gas manifold.

11. The apparatus of claim 10, wherein a common pressure of the first gas manifold is P1, and wherein a third operating mode is provided by ensuring equal pressures Pa>P1 at all of the gas flow Y-junctions, and wherein the on-off valves are used to select a single gas flow to be provided to the gas analysis instrumentation.

12. The apparatus of claim 10, wherein a common pressure of the first gas manifold is P1, and wherein a fourth operating mode is provided by ensuring equal pressures Pa>P1 at all of the gas flow Y-junctions, and wherein the on-off valves are used to select two or more gas flows to be provided to the gas analysis instrumentation in an equal mixture.

13. The apparatus of claim 7, wherein the system controller is configured to measure temperatures at the first gas manifold and at each of the gas flow Y-junctions.

14. The apparatus of claim 13, wherein the system controller is configured to determine one or more relative mass flow rates at one or more of the gas flow Y-junctions from measurements of temperature and pressure.

15. The apparatus of claim 14, wherein the system controller is configured to determine one or more absolute mass flow rates at one or more of the gas flow Y-junctions according to characterization of the one or more of the gas flow Y-junctions.

16. The apparatus of claim 7, further comprising a third gas manifold having one input and two or more outputs, wherein the third manifold is configured to receive the output gas flow of the first gas manifold.

17. The apparatus of claim 16, wherein all of the outputs of the third gas manifold provide the combined gas flow to the gas analysis instrumentation.

18. The apparatus of claim 16, wherein one of the outputs of the third gas manifold is connected to an input of the second gas manifold via a bypass proportional valve, and wherein other outputs of the third gas manifold provide the combined gas flow to the gas analysis instrumentation.

19. The apparatus of claim 18, wherein the system controller is configured to adjust a flow rate of the output gas flow from the first gas manifold without altering a combined gas flow rate provided to the gas analysis instrumentation by adjusting the bypass proportional valve.

* * * * *